United States Patent [19]
Bryans et al.

[11] Patent Number: 6,153,650
[45] Date of Patent: Nov. 28, 2000

[54] SUBSTITUTED GAMMA AMINOBUTYRIC ACIDS AS PHARMACEUTICAL AGENTS

[75] Inventors: Justin Stephen Bryans, Balsham; David Christopher Horwell, Cambridge; Clare Octavia Kneen, Essex, all of United Kingdom; Andrew John Thorpe, Ann Arbor; David Juergen Wustrow, Ann Arbor, both of Mich.

[73] Assignee: Warner-Lambert Company, Morris Plains, N.J.

[21] Appl. No.: 09/254,093

[22] PCT Filed: Oct. 7, 1997

[86] PCT No.: PCT/US97/17997

§ 371 Date: Mar. 1, 1999

§ 102(e) Date: Mar. 1, 1999

[87] PCT Pub. No.: WO98/17627

PCT Pub. Date: Apr. 30, 1998

Related U.S. Application Data

[60] Provisional application No. 60/059,900, Sep. 24, 1997, and provisional application No. 60/029,601, Oct. 23, 1996.

[51] Int. Cl.$^7$ .......................... A01N 37/44; C07C 321/16; C07C 321/28; C07C 229/28

[52] U.S. Cl. .......................... 514/561; 562/431; 562/442; 562/443; 562/444; 562/452; 562/505; 562/507; 562/426; 560/16; 560/17; 560/38; 560/39; 560/121; 560/123; 560/124; 560/125; 514/530; 514/531; 514/538; 514/562; 514/564; 514/567

[58] Field of Search ..................................... 514/530, 531, 514/538, 561, 562, 564, 567; 560/16, 17, 38, 39, 121, 123, 124, 125; 562/426, 431, 442, 443, 444, 452, 505, 506, 507

[56] References Cited

U.S. PATENT DOCUMENTS

| | | | |
|---|---|---|---|
| 4,087,544 | 5/1978 | Satzinger et al. | 424/305 |
| 5,219,886 | 6/1993 | Smith et al. | 514/533 |

FOREIGN PATENT DOCUMENTS

| | | |
|---|---|---|
| 4528769 | 9/1970 | Japan . |
| 9117980 | 11/1991 | WIPO . |
| 9209560 | 6/1992 | WIPO . |
| 9612724 | 10/1994 | WIPO . |
| 9612725 | 10/1994 | WIPO . |
| 9425469 | 11/1994 | WIPO . |

OTHER PUBLICATIONS

Fujii and Yoshifuji, "Lactams. I. Synthesis and acid hydrolysis of 4– and 5–substituted–1–benzyl–2–piperidone derivatives", *Tetrahedron*, vol. 26, No. 24, 1970, pp. 5953–5958.

*Primary Examiner*—Johann Richter
*Assistant Examiner*—Brian J. Davis
*Attorney, Agent, or Firm*—Elizabeth M. Anderson

[57] ABSTRACT

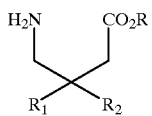

(I)

Novel gamma aminobutyric acids of formula (I) are disclosed and are useful as agents in the treatment of epilepsy, faintness attacks, hypokinesia, cranial disorders, neurodegenerative disorders, depression, anxiety, panic, pain, neuropathological disorders, inflammation, and gastrointestinal damage. Processes for the preparation and intermediates useful in the preparation are also disclosed.

18 Claims, No Drawings

SUBSTITUTED GAMMA AMINOBUTYRIC ACIDS AS PHARMACEUTICAL AGENTS

This application is a 371 of PCT/US97/17997 filed Oct. 7, 1997, which claims priority from provisional application Ser. No. 60/059,900 filed Sep. 24, 1997, and Ser. No. 60/029,601 filed Oct. 23, 1996.

BACKGROUND OF THE INVENTION

Compounds of formula

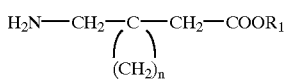

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The compounds of the instant invention are novel substituted gamma aminobutyric acids, their derivatives, pharmaceutically acceptable salts, and prodrugs useful in a variety of disorders. The disorders include: epilepsy, faintness attacks, hypokinesia, cranial disorders, neurodegenerative disorders, depression, anxiety, panic, pain, neuropathological disorders, inflammatory disease, such as arthritis, and gastrointestinal damage such as gastric ulcers, dyspepsia, gastritis, and peptic ulcer.

The compounds of the invention are those of Formula I

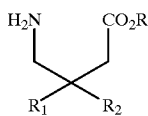

I or a pharmaceutically acceptable salt thereof wherein:
R is hydrogen or lower alkyl;
$R_1$ is hydrogen or lower alkyl;

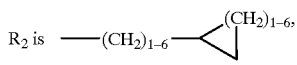

straight or branched alkyl of from 7 to 11 carbon atoms, or
—$(CH_2)_{(1-4)}$—X—$(CH_2)_{(0-4)}$-phenyl wherein
X is —O—, —S—, —$NR_3$— wherein
$R_3$ is alkyl of from 1 to 6 carbons, cycloalkyl of from 3 to 8 carbons, benzyl or phenyl;
wherein phenyl and benzyl can be unsubstituted or substituted with from 1 to 3 substituents each independently selected from alkyl, alkoxy, halogen, hydroxy, carboxy, carboalkoxy, trifluoromethyl, amino, and nitro.

Preferred compounds of the invention are those of Formula I wherein
$R_1$ is hydrogen or methyl; and

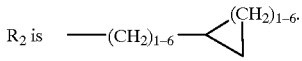

More preferred are those of Formula I wherein $R_1$ is hydrogen or methyl and

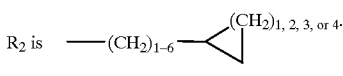

Other preferred compounds of the invention are those of Formula I wherein
$R_1$ is hydrogen or methyl; and
$R_2$ is —$(CH_2)_{1-4}$—X—$(CH_2)_{0-4}$-phenyl.
More preferred are compounds of Formula I wherein $R_2$ is —$(CH_2)_1$—X—$(CH_2)_{0-4}$-phenyl.
Still other preferred compounds of the invention are those of Formula I wherein
$R_1$ is hydrogen or methyl; and
$R_2$ is straight or branched alkyl of from 7 to 11 carbons.
The more preferred compounds of the invention are 3-aminomethyl-4-cyclohexyl-butyric acid and 3-aminomethyl-5-phenyl-pentanoic acid

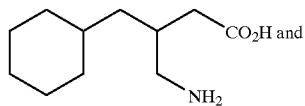

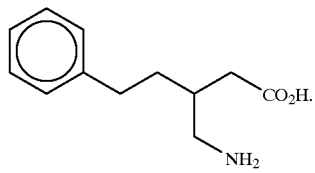

3-Aminomethyl-5-benzylsulfanyl-pentanoic acid;
3-Aminomethyl-5-(4-bromo-benzylsulfanyl)-pentanoic acid;
3-Aminomethyl-5-(3,4-dichloro-benzylsulfanyl)-pentanoic acid;
5-(4-Amino-benzyloxy)-3-aminomethyl-pentanoic acid;
3-Aminomethyl-5-(4-trifluoromethyl-phenylsulfanyl)-pentanoic acid;
3-Aminomethyl-5-p-tolylsulfanyl-pentanoic acid;
3-Aminomethyl-4-[2-(4-chloro-phenyl)-ethylsulfanyl]-butyric acid;
3-Aminomethyl-4-[2-(2,4-dichloro-phenyl)-ethylsulfanyl]-butyric acid;
3-Aminomethyl-4-(4-methyl-benzylsulfanyl)-butyric acid;
3-Aminomethyl-4-(4-bromo-phenylsulfanyl)-butyric acid;
3-Aminomethyl-4-(3,4-dichloro-benzylsulfanyl)-butyric acid; and
3-Aminomethyl-4-(4-tert-butyl-phenoxy)-butyric acid.

The invention also is for pharmaceutical compositions of a compound of Formula I and methods of using the compounds of the invention.

DETAILED DESCRIPTION OF THE INVENTION

The compounds of the instant invention and their pharmaceutically acceptable salts are as defined by Formula I.

The term lower alkyl is a straight or branched group of from 1 to 4 carbons.

The term "alkyl" is a straight or branched group of from 1 to 11 carbon atoms including but not limited to methyl, ethyl, propyl, n-propyl, isopropyl, butyl, 2-butyl, tert-butyl, pentyl, hexyl, and n-hexyl, heptyl, octyl, nonyl, decyl, and undecyl except as where otherwise stated.

The cycloalkyl groups are from 3 to 8 carbons and are cyclopropyl, cyclobutyl, cyclopentyl, cyclohexyl, cycloheptyl, and cyclooctyl.

The benzyl and phenyl groups may be unsubstituted or substituted by from 1 to 3 substituents selected from hydroxy, carboxy, carboalkoxy, halogen, $CF_3$, nitro, alkyl, and alkoxy. Preferred are halogens.

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds may be synthesized by the general route (Scheme I) shown by Silverman R. B., et al., *Synthesis*, 953 (1989), or by a slight modification of this route as outlined in Scheme II. They may also be prepared (Scheme III) via a modification of a scheme outlined by Griffiths G., et al., *Helv. Chim. Acta.* 74:309 (1991). The compounds may also be synthesized by a modification of the methods (Schemes IV and V) outlined by Satzinger G., et al., (U.S. Pat. No. 4,024,175 and U.S. Pat. No. 4,152,326). When $R_1$ is a hydrogen, the compounds may be synthesized (Scheme VI) by the method outlined by Yuen P., et al., *Bioorg. Med. Chem. Lett.*, 4:823 (1994).

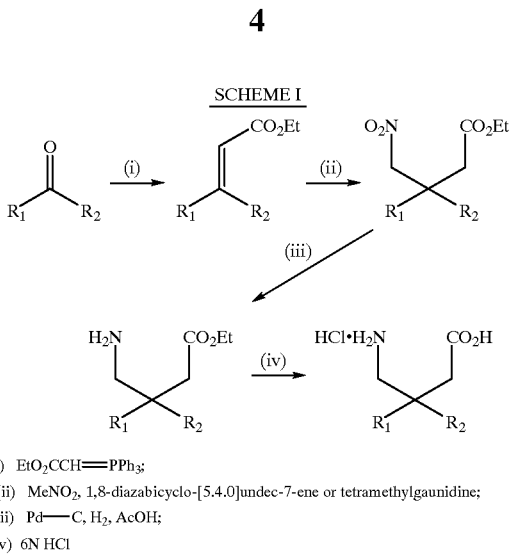

(i) $EtO_2CCH\!=\!\!PPh_3$;
(ii) $MeNO_2$, 1,8-diazabicyclo-[5.4.0]undec-7-ene or tetramethylgaunidine;
(iii) Pd——C, $H_2$, AcOH;
(iv) 6N HCl

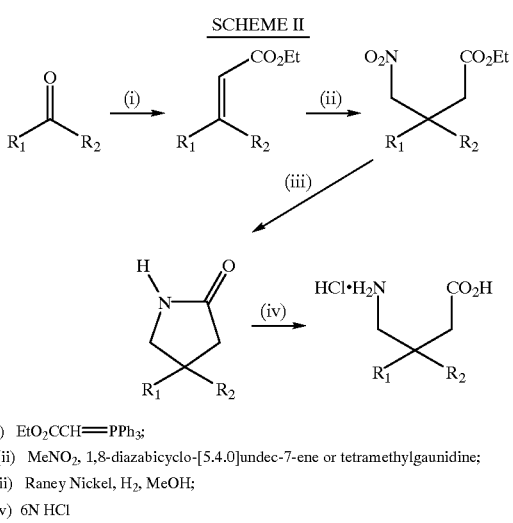

(i) $EtO_2CCH\!=\!\!PPh_3$;
(ii) $MeNO_2$, 1,8-diazabicyclo-[5.4.0]undec-7-ene or tetramethylgaunidine;
(iii) Raney Nickel, $H_2$, MeOH;
(iv) 6N HCl

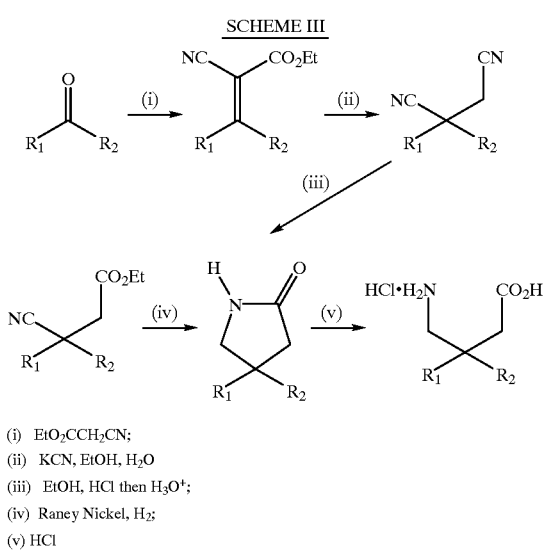

(i) $EtO_2CCH_2CN$;
(ii) KCN, EtOH, $H_2O$
(iii) EtOH, HCl then $H_3O^+$;
(iv) Raney Nickel, $H_2$;
(v) HCl

SCHEME IV
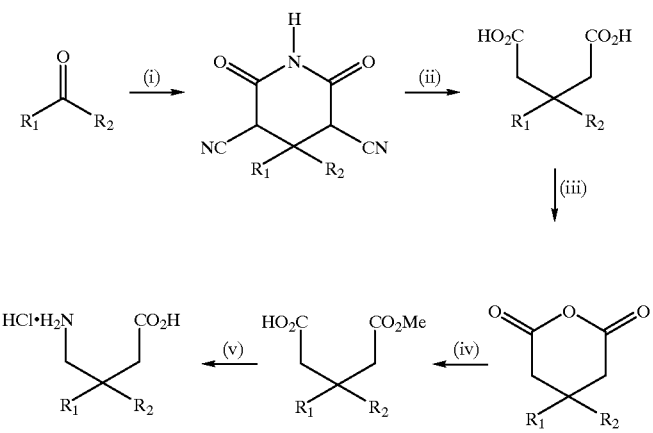
(i) Ethylcyanoacetate, ammonia then $H_3O^+$;
(ii) $H_2SO_4$;
(iii) $Ac_2O$;
(iv) MeOH, NaOMe
(v) (a) EtOCOCl, $Et_3N$; (b) $NaN_3$; (c) Heat; (d) HCl
SCHEME V
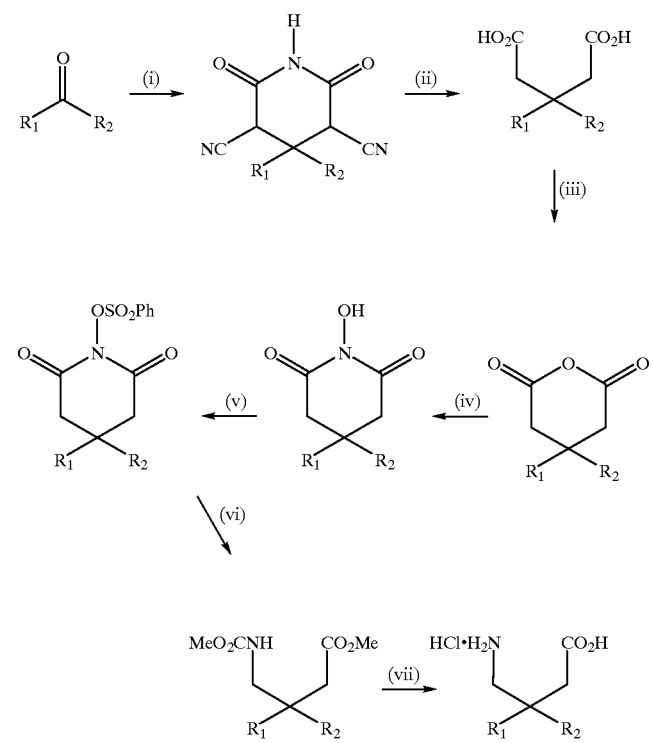
(i) Ethylcyanoacetate, ammonia then $H_3O^+$;
(ii) $H_2SO_4$;
(iii) $Ac_2O$;
(iv) $H_2NOH$;
(v) $PhSO_2Cl$;
(vi) $Et_3N$, MeOH;
(vii) HCl

SCHEME VI

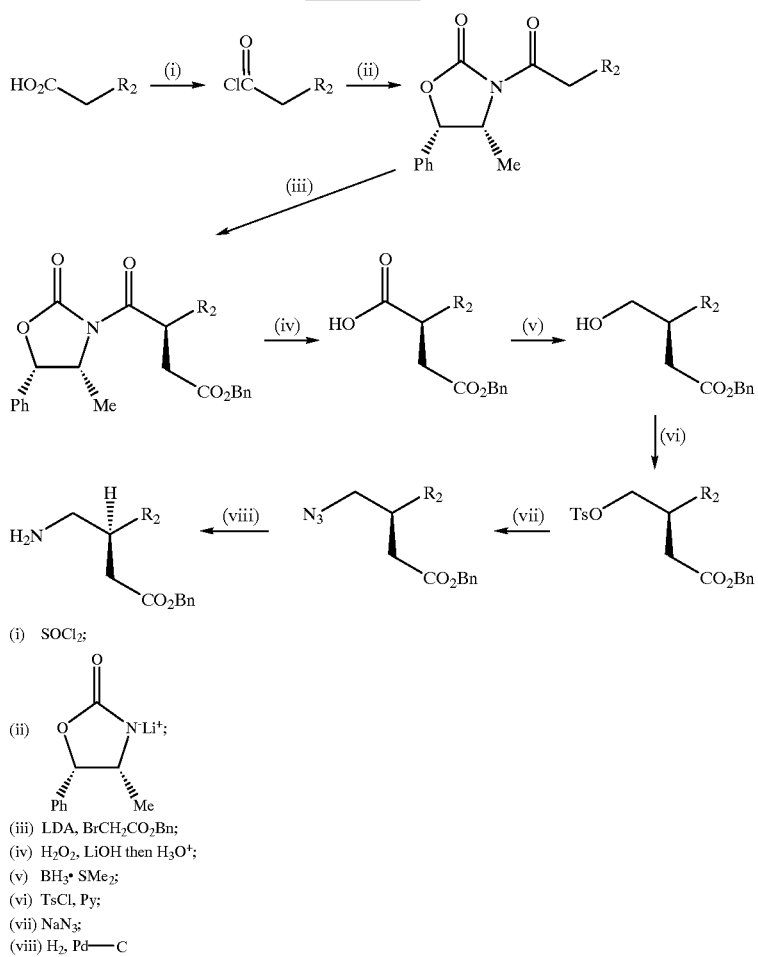

(i) SOCl$_2$;

(ii) 
(oxazolidinone with N-Li$^+$, Ph, Me);

(iii) LDA, BrCH$_2$CO$_2$Bn;
(iv) H$_2$O$_2$, LiOH then H$_3$O$^+$;
(v) BH$_3$•SMe$_2$;
(vi) TsCl, Py;
(vii) NaN$_3$;
(viii) H$_2$, Pd—C

SCHEME VII
Synthesis of 3-Aminomethyl-4-cyclobutyl-butyric Acid Hydrochloride

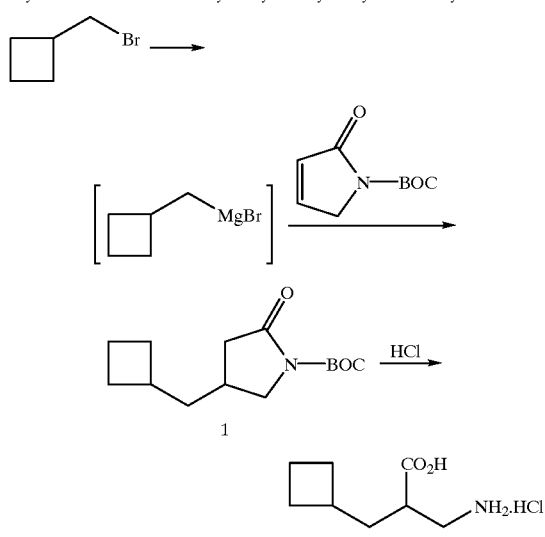

SCHEME VIII
Synthesis of 3-Aminomethyl-4-cyclopropyl-butyric Acid

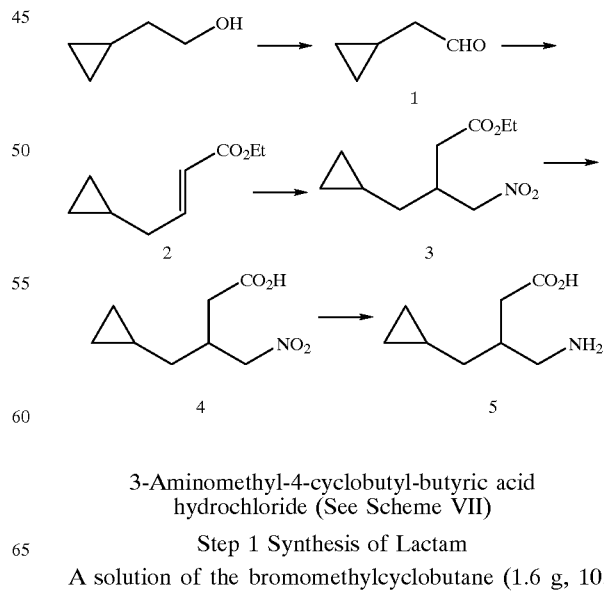

3-Aminomethyl-4-cyclobutyl-butyric acid hydrochloride (See Scheme VII)

Step 1 Synthesis of Lactam

A solution of the bromomethylcyclobutane (1.6 g, 10.9 mmol) in THF (10 mL) is added with stirring to a suspension of magnesium turnings in THF (5 mL). The reaction is heated to reflux for 10 minutes. The reaction is cooled to 0° C. and copper bromide dimethylsulfide complex (1.1 g, 5.4 mmol) is added. The solution is cooled to −78° C. and is treated with 1,1-dimethylethyl 2,5-dihydro-2-oxo-1H-pyrrole-1-carboxylate (1.0 g, 5.4 mmol), and the reaction is stirred at this temperature for 15 minutes. The reaction is quenched with saturated aqueous ammonium chloride and allowed to warm to room temperature. The THF is removed under reduced pressure, and the resulting aqueous mixture is extracted with ethyl acetate. The organic layer is washed with brine, dried over sodium sulfate, and the solvent is removed under reduced pressure. The resulting residue is chromatographed over silica gel (3:1 hexane:ethyl acetate as the eluents) to give the intermediate lactam 1.

Step 2 Lactam Hydrolysis

A mixture of lactam 1 (0.6 g, 2.3 mmole) was warmed to reflux in 50 mL of 6N HCl for 18 hours. The water was evaporated, and the resulting residue was recrystallized from ethyl acetate to give the desired product 3-aminomethyl-4-cyclobutyl-butyric acid hydrochloride as white solid, MP 95° C.

NMR (400 MHz, DMSO): δ 7.8 (bs, 2H), 2.7 (d, 2H), 2.3 (m, 2H), 2.15 (m, 1H), 1.9 (m, 3H), 1.7 (m, 2H), 1.4, (m, 5H). Analysis calculated for ($C_9H_{17}NO_2 \cdot HCl$): C, 52.03; H, 8.75; N, 6.74. Found: C, 51.46; H, 8.53; N, 6.62.

3-Aminomethyl-4-cyclopropyl-butyric acid (See Scheme VIII)

Step 1 Oxidation of 2-Cyclopropyl-ethanol

Pyridinium chlorochromate (26.3 g, 121.9 mmol) and neutral alumina (92.85 g, 906.9 mmol) are stirred at room temperature in 500 mL of methylene chloride under Ar for 15 minutes. 2-Cyclopropyl-ethanol (7.0 g, 81.3 mmol) in 100 mL of methylene chloride is added to the mixture at room temperature, and the reaction mixture is stirred for 3 hours. The solids are removed by filtration through silica gel and washed with methylene chloride. Evaporation of the eluate gives 4.2 g of 2-cyclopropyl-acetaldehyde as a clear oil.

Step 2 Formation of Unsaturated Ester 2

Triethyl phophonoacetate (10.9 g, 48.7 mmol) is added to a suspension of NaH (1.2 g, 48.7 mmole) in DME at 0° C. under Ar, and the mixture is stirred for 10 minutes. 2-Cyclopropyl-acetaldehyde (4.1 g, 48.7 mmol) is added, and the reaction mixture is warmed to reflux for 3 hours. The cooled solution is evaporated, and the residue is taken up in 100 mL of $H_2O$. The organics are extracted into hexane (3×150 mL), and the combined hexane extracts are dried over $Na_2SO_4$. Evaporation of the solvent gives 3.4 g of 4-cyclopropyl-2-butenoic acid ethyl ester as a yellow oil.

Step 3 Addition of Nitromethane to Unsaturated Ester 2

DBU (4.1 g, 26.9 mmol) is added to a solution of 4-cyclopropyl-2-butenoic acid ethyl ester (3.4 g, 26.9 mmol) and nitromethane (9.13 g, 135 mmol) in 20 mL of $CH_3CN$. The solution is warmed to 60° C. under Ar for 4 hours, then stirred at room temperature overnight. The $CH_3CN$ is evaporated, and the residue is taken up in 50 mL of EtOAc. The solution is washed with saturated $KH_2PO_4$ (3×50 mL) followed by 50 mL of brine. The organic layer is dried over $Na_2SO_4$ and evaporated to give an oil which is chromatographed (MPLC) over silica gel with 25% EtOAc/hexane to give 2.4 g of 4-cyclopropyl-3-nitromethyl-butanoic acid ethyl ester 3.

Step 4 Hydrolysis of ester 3

A solution of 4-cyclopropyl-3-nitromethyl-butanoic acid ethyl ester (1.34 g, 7.27 mmol) in 50 mL of MeOH is added to 10 mL of 10% $KOH/H_2O$ at room temperature and stirred overnight. The MeOH is evaporated, and the pH of the solution is adjusted to ca. 7 by the addition of $KH_2PO_4$. The aqueous solution is extracted with EtOAc (3×100 mL), and the combined extracts are dried over $Na_2SO_4$. Evaporation of the solvents gives 1.3 g of 4-cyclopropyl-3-nitromethyl-butanoic acid as a white solid.

Step 5 Reduction of Nitro Acid 4

A solution of the nitro acid (0.85 g, 4.5 mmol) is dissolved in 2M ammonium hydroxide, treated with Raney nickel, and placed under 50 psi hydrogen for 18 hours. The solution is filtered and evaporated, and the resulting residue is triturated with acetonitrile, the residue is dissolved in MeOH (25 mL), filtered through celite, evaporated, triturated with ether, and filtered to give 3-aminomethyl-4-cyclopropyl-butyric acid as a white solid (0.47 g, 66% yield), MP 172–173° C.

NMR (400 MHz, DMSO): δ 2.9 (d, 1H), 2.6 (m, 1H), 2.3 (d, 1H), 2.2 (dd, 1H), 1.9 (t, 1H), 1.1 (t, 2H), 0.7 (m, 1H), 0.4 (dd, 2H), 0.1 (dd, 2H). Analysis calculated for ($C_8H_{15}NO_2$): C, 61.12; H, 9.62; N, 8.91. Found: C, 60.83; H, 9.46; N, 8.66.

SCHEME IX

Approach to Racemic Ethers and Thioether Analogs

-continued

R₁ = benzyl, phenyl substituted benzyl, substituted phenyl
X = O or S

Target molecules

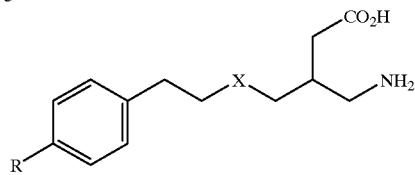

where R = Br, Cl, H, Me
X = O or S c.f.

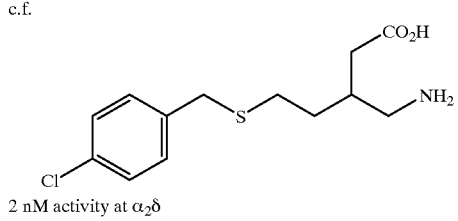

2 nM activity at α₂δ

Other targets are the analogs below

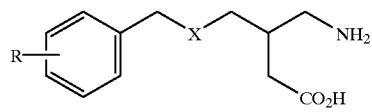

X = S or O

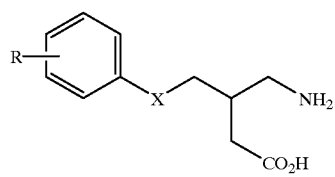

where R = Br, Cl, H, Me, NH₂, MeO
X = O or S

SCHEME X
Lactam Approach to Homocysteine Analogs

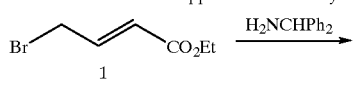

$\xrightarrow{\text{H}_2\text{NCHPh}_2}$

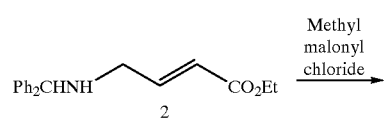

$\xrightarrow{\text{Methyl malonyl chloride}}$

-continued

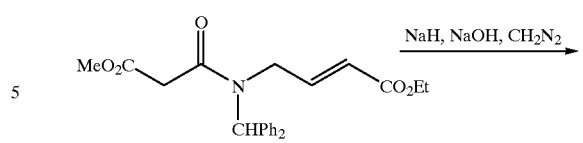

$\xrightarrow{\text{NaH, NaOH, CH}_2\text{N}_2}$

3

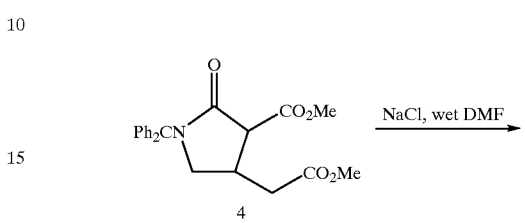

$\xrightarrow{\text{NaCl, wet DMF}}$

4

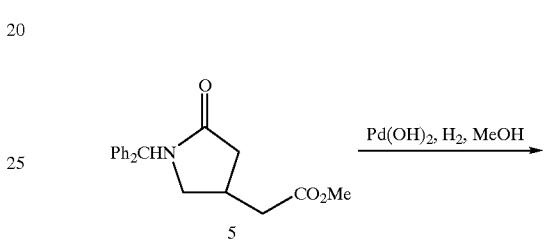

$\xrightarrow{\text{Pd(OH)}_2, \text{H}_2, \text{MeOH}}$

5

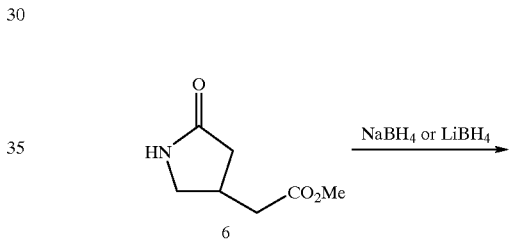

$\xrightarrow{\text{NaBH}_4 \text{ or LiBH}_4}$

6

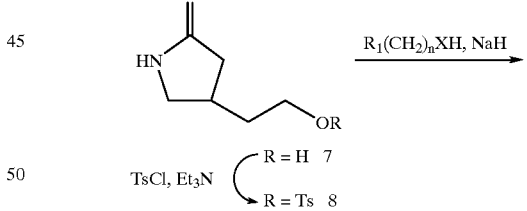

$\xrightarrow{R_1(CH_2)_nXH, \text{NaH}}$

R = H  7
TsCl, Et₃N
R = Ts  8

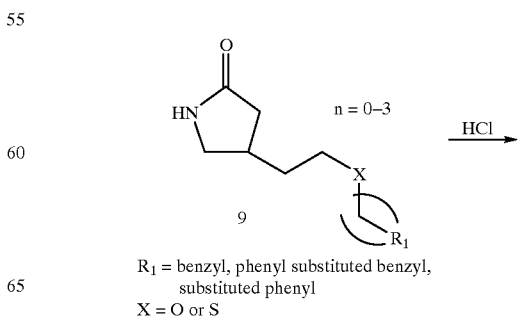

n = 0–3
$\xrightarrow{\text{HCl}}$

9

R₁ = benzyl, phenyl substituted benzyl, substituted phenyl
X = O or S

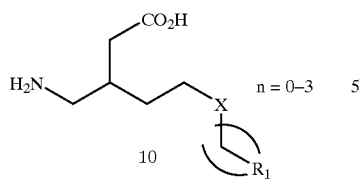
SCHEME XI
Linear Approach to Chiral and Thioethers
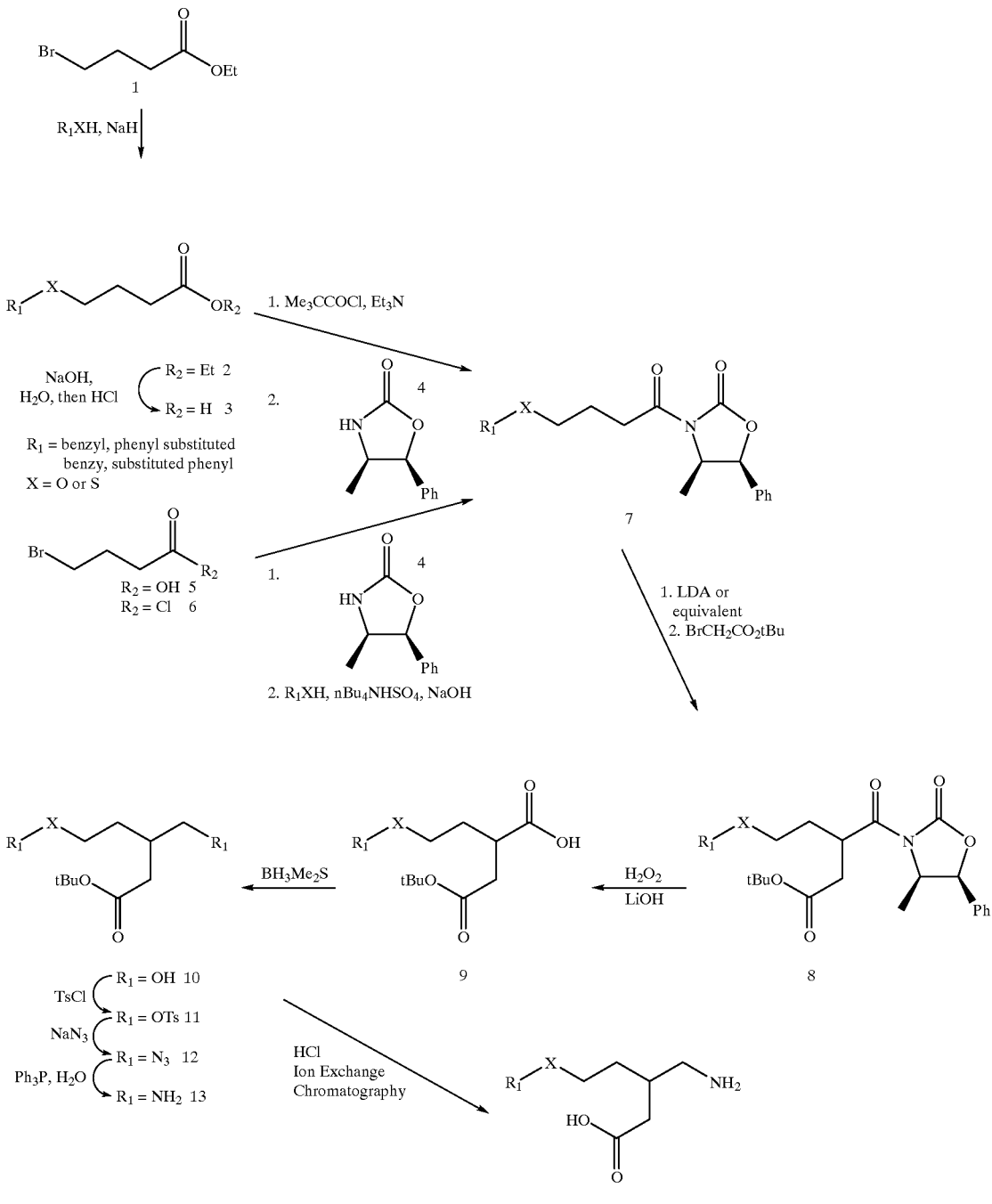

Target molecules

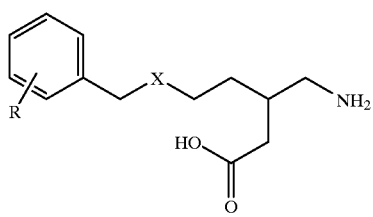

where R = 4-H, 4-Cl, 4-Br, 4-NH$_2$, 4-MeO
X = O or S

-continued

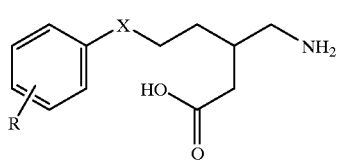

where R = 4-H, 4-Cl, 4-Br, 4-NH$_2$, 4-MeO
X = O or S

Synthesis of Compounds in Scheme IX

Compounds of structure 4, where X is defined as O or S, can be prepared by refluxing compounds of structure 3 in an aqueous acid such as 6N hydrochloric acid, and the resulting amino acid hydrochloride can be converted to the amino acid using an ion exchange resin.

Compounds of structure 3, where X is defined as above, are prepared from a compound of structure 2 by reacting structure 2 with an appropriate alkoxide, phenoxide, thioalkoxide, or thiophenoxide anion generated from the appropriate alcohol, phenol, thiol, or thiophenol with a base such as sodium hydride in a solvent such as tetrahydrofuran.

A compound of structure 2 can be prepared from compound 1 by reduction of compound 1 (U.S. Pat. No. 4,113,874) with a hydride reducing agent such as lithium borohydride and in a separate step treating the reduced product with tosylchloride and a tertiary amine base such as triethylamine in a solvent such as tetrahydrofuran.

Synthesis of Compounds in Scheme X

Compounds of structure 10, where X is defined as O or S, can be prepared from compounds of structure 9 in the presence of an acid such as, for example, concentrated hydrochloric acid and the like to give compounds of structure 10. Preferably, the reaction is carried out in the presence of concentrated hydrochloric acid between room temperature and reflux. Isolation of the free base can be achieved through treatment of the salt of structure 10 with a ion-exchange resin.

Compounds of structure 9, where X is defined as above, can be prepared from a compound of structure 8, in the presence of a mercaptan, alcohol, thiophenol, or phenol in a solvent such as tetrahydrofuran and the like, in the presence of a base such as sodium hydride and the like, to give a compound of structure 9. Preferably the reaction is carried out through reaction of a compound of structure 8 with a suitable mercaptan or alcohol in the presence of sodium hydride in tetrahydrofuran at temperature between 0° C. and reflux.

A compound of structure 8 can be prepared from a compound of structure 7, where X is defined as above, in the presence of sulfonylchloride, such as mesyl chloride, p-toluenesulfonyl chloride, and a base such as triethylamine and the like, and a solvent such as dichloromethane and the like to give a compound of structure 8. Preferably, the reaction is carried out in the presence of p-toluene sulfonyl chloride and triethylamine in methylene chloride between 0° C. and the temperature of reflux.

A compound of structure 7 can be prepared from a compound of structure 6 in the presence of a borohydride such as sodium borohydride, lithium borohydride, and the like in a solvent such as tetrahydrofuran or ethylene glycol dimethyl ether, and the like to give after treatment of the intermediate with an acid such as, for example, aqueous hydrochloric acid and citric acid and the like to give a compound of structure 7. Preferably, the reaction is carried out in the presence of sodium borohydride in tetrahydrofuran followed by treatment with aqueous hydrochloric acid.

A compound of structure 6 can be prepared from a compound of structure 5 in the presence of a palladium metal catalyst such as, for example, palladium hydroxide on carbon and the like in a solvent such as, for example, methanol or ethanol in a hydrogen atmosphere to give a compound of structure 6. Preferably, the reaction is carried out in the presence of palladium hydroxide in methanol under a hydrogen atmosphere between 50 and 500 psi according to the method of Carruthers N. I., Wong S-C., and Chan T-M., *J. Chem. Research*, (S):430–431 (1996).

A compound of structure 5 can be prepared from a compound of structure 4 in the presence of a metal chloride such as, for example, sodium chloride and the like in aqueous dimethylformamide and the like to give a compound of structure 5 (Galeazzi R., Geremia S., Mobbili G., Orena M., *Tetrahedron: Asymmetry*, 7(1):79–88 (1996)). Preferably, the reaction is carried out in the presence of sodium chloride in wet dimethylformamide at a temperature between 0° C. and the temperature of reflux.

A compound of structure 4 can be prepared from a compound of structure 3 following the procedure described in the literature (Galeazzi R., supra., 1996) to give a compound of structure 4. Preferably, according to the procedure described (Galeazzi R., supra., 1996), the reaction is carried out in the presence of sodium hydride in tetrahydrofuran followed by complete hydrolysis of the intermediate mixture of methyl carboxylate and acid with sodium hydroxide followed by treatment of the acid with diazomethane.

A compound of structure 3 can be prepared from a compound of structure 2 in the presence of an acid chloride such as, for example, methyl malonyl chloride and the like and a base such as, for example, triethylamine to give a compound of structure 3. Preferably, the reaction is carried out in the presence of methyl malonyl chloride, triethylamine, and N,N-dimethylamino pyridine in dichloromethane between 0° C. and the temperature of reflux.

A compound of structure 2 can be prepared from a compound of structure 1 such as, for example, commercially available ethyl 4-bromocrotonate or any 4-halocrotonate in the presence of a suitably protected amine such as, for example, benzylamine, α-methylbenzylamine or commercially available aminodiphenylmethane to give a compound of structure 2. Preferably, the reaction is carried out in dichloromethane at room temperature according to the procedure of Cardillo B., Galeazzi R., Mobbili G., Orena M., and Rossetti M., *Heterocycles*, 38(12):2663–2676 (1994).

Synthesis of Compounds in Scheme XI

Compounds of structure 14, where X is defined as above, can be prepared from a compound of structure 13 in the presence of an acid such as, for example, hydrochloric acid and the like to give a compound of structure 14 following ion-exchange chromatography. Preferably, the reaction can be carried out with 6N hydrochloric acid and the resultant hydrochloride salt converted into the amine 14 using an ion-exchange resin.

Compounds of structure 13, where X is defined as above, can be prepared from compounds of structure 12 in the presence of triphenylphosphine and the like in a solvent such as water to give compounds of structure 13.

Compounds of structure 12, where X is defined as above, can be prepared from compounds of structure 11 in the presence of sodium azide in a solvent such as dimethyl sulphoxide, water, and the like to give compounds of structure 12. Preferably, the reaction can be carried out using sodium azide in dimethyl sulphoxide at temperatures between room temperature and reflux following conditions described in the literature (Yuen P-W., Kanter G. D., Taylor C. P., and Vartanian M. G., *Bioorganic and Medicinal Chem. Lett.*, 4(6):823–826 (1994)).

Compounds of structure 11, where X is defined as above, can be prepared from those of structure 10 in the presence of a sulfonyl chloride such as, for example, tosyl, mesyl chloride, and the like in a solvent such as pyridine or dichloromethane and triethylamine to give compounds such as structure 11. Preferably, the reaction can be carried out at room temperature in dichloromethane using triethylamine as an acid scavenger.

Compounds of structure 10, where X is defined as above, can be prepared from compounds of structure 9 in the presence of a borane derived reducing agent such as, for example, borane dimethylsulphide and the like, in a solvent such as tetrahydrofuran between a temperature of –78° C. to room temperature. Preferably, the reaction can be carried out according to literature procedures in the presence of borane dimethylsulphide in tetrahydrofuran at room temperature.

Compounds of structure 9, where X is defined as above, can be prepared from compounds of structure 8 in the presence of base such as lithium hydroxide, hydrogen peroxide in a solvent such as water or tetrahydrofuran to give compounds of structure 9. Preferably, the reaction can be carried out using hydrogen peroxide and lithium hydroxide in aqueous tetrahydrofuran at 0° C. according to the method described in the literature (Yuen P-W., supra., 1994).

Compounds of structure 8, where X is defined as above, can be prepared from compounds of structure 7 in the presence of a suitably derived ester of bromoacetic acid such as, for example, t-butyl bromoacetate, benzyl bromoacetate with an organometallic base such as, for example, lithium diisopropylamide or lithium bis(trimethylsilyl)amide and the like in a solvent such as, for example, tetrahydrofuran, ether and the like to give compounds of structure 8. Preferably, the reaction can be carried out using lithium diisopropylamide in tetrahydrofuran at –78° C. and treatment of the resultant anion intermediate with t-butylbromoacetate at –78° C. to –30° C.

Compounds of structure 7, where X is defined as above, can be prepared from compounds of structure 3 in the presence of trimethylacetylchloride and a base such as, for example, triethylamine in a solvent such as, for example, tetrahydrofuran, and treatment of the intermediate with the oxazolidinone of structure 4 and lithium chloride to give compounds of structure 7. Preferably, the reaction is carried out by treating compounds of structure 3 to trimethylacetylchloride and triethylamine in tetrahydrofuran at –20° C. followed by treatment of the intermediate with the oxazolidinone 4 and lithium chloride at room temperature according to literature procedures (Ho G-J. and Mathre D. J., *J. Org. Chem.*, 60:2271–2273, (1995)).

Alternatively, compounds of structure 7 can be prepared from compounds of structure 6 in the presence of the oxazolidinone of structure 4 and a base such as, for example, sodium hydride in a solvent such as tetrahydrofuran. The resultant intermediate adduct can be treated in situ with various phenols, alcohols, thiols and thiophenols under phase transfer conditions to give compounds of structure 7. Preferably, the reaction is carried out according to literature procedures (Holla E. W., Napierski B., Rebenstock H-P., *Synlett.*, 333–334 (1994)).

Compounds of structure 3 can be prepared from compounds of structure 2 in the presence of a base such as, for example, sodium or potassium hydroxide in aqueous alcohol such as, for example, methanol or ethanol to give compounds of structure 3 following acidification and isolation of the acid. Preferably, the reaction is carried out by treatment of compounds of structure 6 with 50% sodium hydroxide in aqueous methanol at reflux.

Compounds of structure 2 can be prepared from a compound of structure 1 in the presence of various alcohols, phenols, thiols, and thiophenols such as, for example, benzyl alcohol, phenol, benzylmercaptan and a base such as, for example, sodium or potassium hydride in a solvent such as, for example, tetrahydrofuran or ether, to afford compounds of structure 2. Preferably, the reaction can be carried out through the treatment of commercially available ethyl-4-bromobutyrate 1 with preformed sodium anions of various oxygen or sulfur based nucleophiles in tetrahydrofuran at room temperature.

Compounds of structure 6 can be formed from compounds of structure 5 in the presence of thionyl chloride. Preferably, commercially available halides such as 4-bromobutyric acid 5 are treated with excess thionyl chloride at reflux to give compounds of structure 6.

Selected examples prepared by the above methods include but are not limited to:

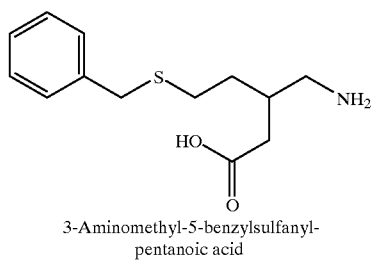

3-Aminomethyl-5-benzylsulfanyl-pentanoic acid

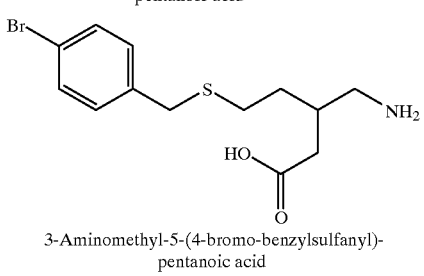

3-Aminomethyl-5-(4-bromo-benzylsulfanyl)-pentanoic acid

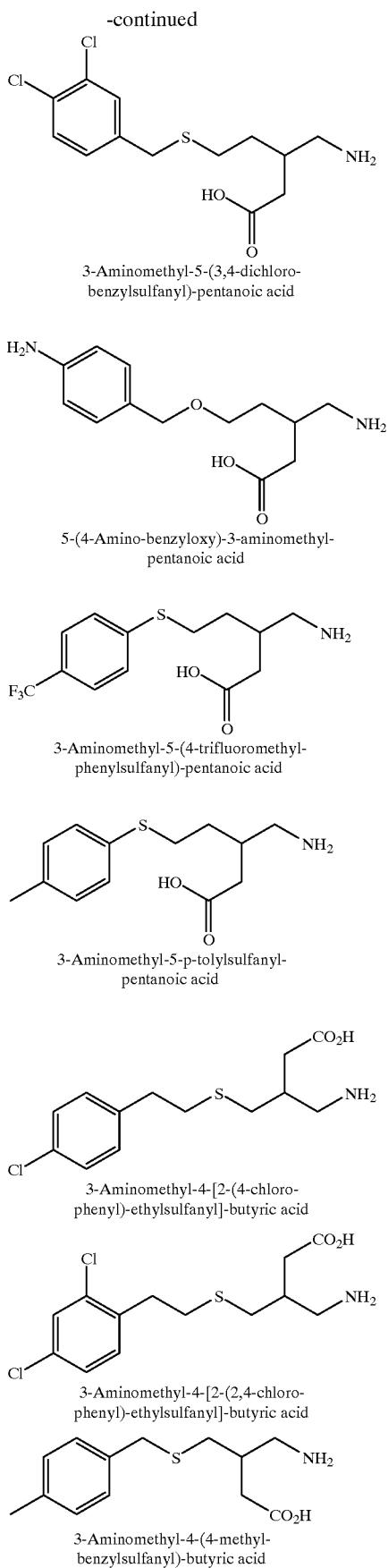

3-Aminomethyl-5-(3,4-dichloro-benzylsulfanyl)-pentanoic acid 5-(4-Amino-benzyloxy)-3-aminomethyl-pentanoic acid 3-Aminomethyl-5-(4-trifluoromethyl-phenylsulfanyl)-pentanoic acid 3-Aminomethyl-5-p-tolylsulfanyl-pentanoic acid 3-Aminomethyl-4-[2-(4-chloro-phenyl)-ethylsulfanyl]-butyric acid 3-Aminomethyl-4-[2-(2,4-chloro-phenyl)-ethylsulfanyl]-butyric acid 3-Aminomethyl-4-(4-methyl-benzylsulfanyl)-butyric acid

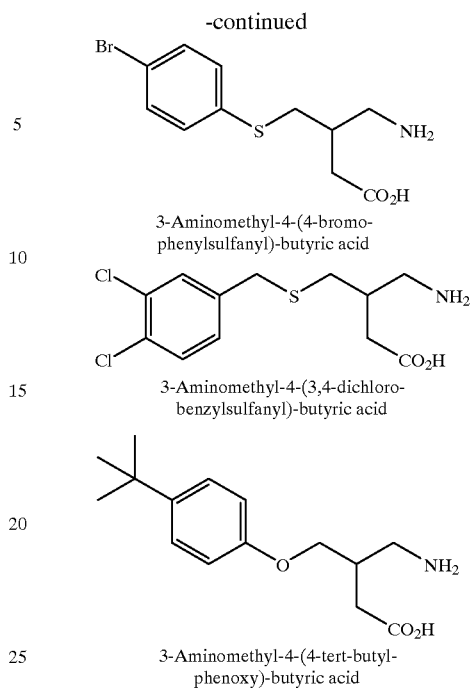

3-Aminomethyl-4-(4-bromo-phenylsulfanyl)-butyric acid

3-Aminomethyl-4-(3,4-dichloro-benzylsulfanyl)-butyric acid

3-Aminomethyl-4-(4-tert-butyl-phenoxy)-butyric acid

The radioligand binding assay using [$^3$H]gabapentin and the $\alpha_2\delta$ subunit derived from porcine brain tissue was used ("The Novel Anti-convulsant Drug, Gabapentin, Binds to the $\alpha_2\delta$ Subunit of a Calcium Channel", Gee N., et al., *J. Biological Chemistry*, in press).

Biological Data

[$^3$H]gabapentin Binding Assay

1. Preparation of Brain Membranes

Pig brain cortex (up to 35 g) is homogenized in 10 volumes of buffer A (0.32 M Sucrose/1 mM EDTA/1 mM EGTA/0.1 mM PMSF/10 mM Hepes/KOH, pH 7.4, 4° C.) by six strokes of a glass/teflon homogenizer at 600 rpm. After removal of the 1000 $g_{max}\times10$ min pellet, the supernatant is centrifuged at 40,000 $g_{max}$ for 20 minutes and the resulting pellet resuspended in 10 volumes of buffer B (Buffer A without sucrose). Following 30 minutes of continuous stirring, membranes are pelleted as above and resuspended in 3 volumes of buffer C (1.00 mM EDTA/1.00 mM EGTA/20% glycerol/0.1 mM PMSF/10 mM Hepes/KOH, pH 7.4, 4° C.). Aliquots of 1 or 2 mL are frozen at −70° C. The protein concentration of the membrane preparation is usually between 5 and 6 mg/mL.

2. Binding Assay Protocol

A curve of [$^3$H]gabapentin binding versus protein concentration is performed with each preparation of membranes. A protein concentration (usually between 30 and 50 μg per tube) in the linear part of the curve is used in the binding assay.

Binding of [$^3$H]gabapentin to membranes is carried out at 22° C. in 10 mM Hepes/KOH, pH 7.4, 22° C. for 40 minutes. Assay tubes contain 25 μL drug, 25 μL of [$^3$H]gabapentin (final assay concentration 10 nM), and 200 μL protein in a final volume of 250 μL. Nonspecific binding is that obtained in the presence of 10 μM (S+)-3-isobutyl GABA. Separation of bound and free ligand is effected by rapid filtration through GF/B filters presoaked briefly in the wash buffer. Filters are washed with 3×4 mL of cold 50 mM Tris/HCl, pH 7.4 (4° C.), and counted in a TopCount scintillation counter after a period of 12 hours.

3. Data Analysis

The analysis system is based on two software packages, GraphPad Prism and Microsoft Excel. Raw counter data are processed in an Excel template and then exported to Prism for nonlinear regression analysis. The results from Prism are exported back to Excel where goodness-of-fit and other related tests are applied.

| [³H]Gabapentin Binding Compound | Binding (IC$_{50}$, µM) |
|---|---|
| 3-Aminomethyl-4-cyclobutyl-butyric acid Hydrochloride | 0.407 |
| 3-Aminomethyl-4-cyclohexyl-butyric acid Hydrochloride | 4.87 |

The compounds of the invention show good binding affinity to the $\alpha_2\delta$ subunit. Gabapentin (Neurontin®) is about 0.10 to 0.12 µM in this assay. Since the compounds of the instant invention also bind to the subunit, they are expected to exhibit pharmacologic properties comparable to gabapentin. For example, as agents for convulsions, anxiety, and pain.

The compounds of the invention are related to Neurontin®, a marketed drug effective in the treatment of epilepsy. Neurontin® is 1-(aminomethyl)-cyclohexaneacetic acid of structural formula

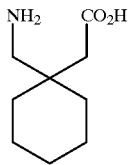

The compounds of the invention are also expected to be useful in the treatment of epilepsy.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia such as in a patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, and hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-Induced Hyperalgesia

Nociceptive pressure thresholds were measured in the rat paw pressure test using an analgesymeter (Randall-Sellitto Method: Randall L. O., Sellitto J. J., A method for measurement of analgesic activity on inflamed tissue. Arch. Int. Pharmacodyn., 4:409–419 (1957)). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 µL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5, and 5 hours post carrageenin.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2.0 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 mL/kg for rats and marmosets and 10 mL/kg for mice.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., Exploration of mice in a black and white box: validation as a model of anxiety. *Pharmacol. Biochem. Behav.*, 32:777–785 (1989)).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 28:901–905 (1989)).

Rat Elevated X-Maze

A standard elevated X-maze (Handley S. L., et al., Effects of alpha-adrenoceptor agonists and antagonists in a maze-exploration model of 'fear'-motivated behavior. *Naunyn-Schiedeberg's Arch. Pharmacol.*, 327:1–5 (1984)), was automated as previously described (Field, et al., Automation of the rat elevated X-maze test of anxiety. *Br. J. Pharmacol.*, 102(Suppl):304P (1991)). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 96(Suppl):312P (1989)).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 5:7–9 (1995)).

The compounds of the instant invention are also expected to be useful in treating the symptoms of manic, acute or chronic, single upside, or recurring. They are also expected to be useful in treating and/or preventing bipolar disorder U.S. Pat. No. 5,510,381).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the instant invention; they are not intended to limit the scope.

EXAMPLE 1

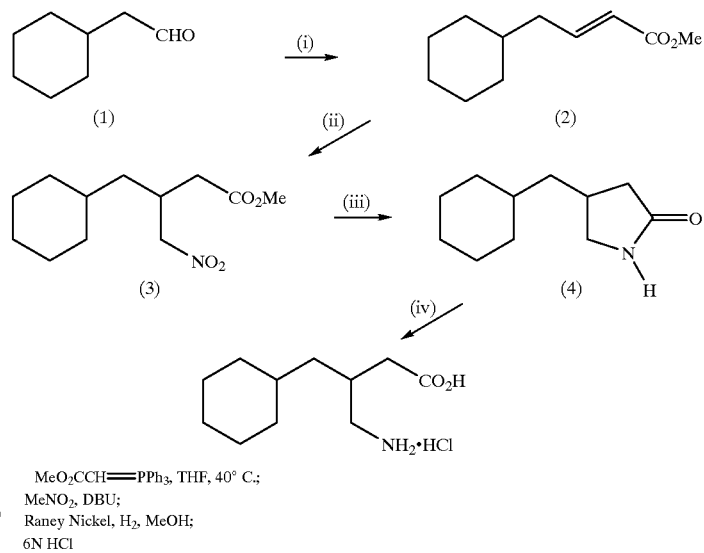

(i) MeO$_2$CCH═PPh$_3$, THF, 40° C.;
(ii) MeNO$_2$, DBU;
(iii) Raney Nickel, H$_2$, MeOH;
(iv) 6N HCl Synthesis of the Unsaturated Ester (2)

The aldehyde (1) (1.035 g, 8.2 mmol) was dissolved in dry tetrahydrofuran (THF) (20 mL) and stirred with methyl (triphenylphosphoranylidene) acetate (2.51 g, 7.5 mmol) under reflux. After 4.5 hours the solvent was removed in vacuo and the residue stirred with heptane (50 mL). After 30 minutes the solid was removed by filtration and washed with heptane (3×30 mL). The filtrate and washings were combined and the solvent removed in vacuo to give an oil. This was purified by flash chromatography (silica, ethyl acetate/heptane 1/9) to give 1.06 g (77%) of (2) as a colorless oil.

$^1$H NMR (400 MHz) (CDCl$_3$): δ 0.80–1.02 (2H, m), 1.08–1.35 (5H, m), 1.35–1.53 (4H, m), 2.09 (2H, m), 3.72 (3H, s), 5.80 (1H, d, J=14 Hz), 6.95 (1H, m). MS (CI$^+$)(m/z): 183 (MH$^+$, 100%), 141 (65%), 111 (100%). IR (thin film) (cm$^{-1}$) v: 1166, 1209, 1268, 1448, 1656, 1727, 2852, 2923.

Synthesis of the Nitroester (3)

The unsaturated ester (2) (500 mg, 2.7 mmol) was dissolved in nitromethane (5 mL) with 1,8-diazabicyclo[5.4.0]undec-7-ene (411 μL, 2.7 mmol) and stirred at room temperature. After 66 hours the mixture was diluted with diethyl ether (30 mL) and washed with water (30 mL) followed by 2N HCl (20 mL). The ether layer was separated, dried (MgSO$_4$), and the solvent removed in vacuo. The residue was purified by flash chromatography (silica, ethyl acetate/heptane 1:1) to give 0.422 g (63%) of (3) as a colorless oil.

$^1$H NMR (400 MHz) (CDCl$_3$): δ 0.80–0.98 (2H, m), 1.07–1.35 (6H, m), 1.63–1.75 (5H, m), 2.44 (2H, d, J=6 Hz), 2.72 (1H, m), 3.70 (3H, s), 4.46 (2H, m). MS (CI$^+$)(m/z): 244 (MH$^+$, 100%), 226 (63%), 212 (100%). IR (thin film) (cm$^{-1}$)v: 843, 891, 971, 1004, 1065, 1179, 1384, 1435, 1557, 1732, 2852, 2923.

Synthesis of the Lactam (4)

The nitro ester (3) (400 mg, 1.65 mmol) was dissolved in methanol (30 mL) and shaken over Raney Nickel (catalytic, prewashed with methanol) under an atmosphere of hydrogen gas (47 psi) at 30° C. After 18 hours the catalyst was filtered off and the solvent removed in vacuo. The residue was purified by flash chromatography (silica, ethyl acetate/n-pentane 3:7) to give 210 mg (70%) of (4) as a colorless oil.

$^1$H NMR (400 MHz) (CDCl$_3$): δ 0.80–0.98 (2H, m), 1.07–1.43 (7H, m), 1.53–1.75 (4H, m), 1.97 (1H, dd, J=16, 8 Hz), 2.41 (1H, dd, J=16, 8 Hz), 2.59 (1H, m), 2.99 (1H, m), 4.47 (1H, m), 5.43 (1H, br s). MS (CI$^+$)(m/z): 182 (MH$^+$, 100%).

Synthesis of 3-aminomethyl-4-cyclohexyl-butyric acid

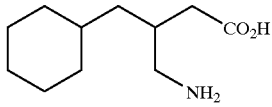

The lactam (4) (197 mg, 1.1 mmol) was heated to reflux in 6N HCl (15 mL). After 6 hours the mixture was cooled to room temperature and the solvent removed in vacuo. The residue was triturated with ethyl acetate to yield a white solid which was collected and dried to give 113 mg (44%) of the product as a white powder.

$^1$H NMR (400 MHz) (d$_6$-DMSO): δ 0.75–0.90 (2H, m), 1.04–1.35 (6H, m), 1.57–1.72 (5H, m), 2.14 (1H, m), 2.21 (1H, dd, J=16, 8 Hz), 2.40 (1H, dd, J=16, 8 Hz), 2.75 (2H, d, J=6 Hz), 7.94 (3H, br s). IR (thin film) (cm$^{-1}$) v: 1712, 2922. Microanalysis calculated for C$_{11}$H$_{22}$NO$_2$Cl: C, 56.04; H, 9.41; N, 5.94; Cl, 15.04. Found: C, 56.21; H, 9.16; N, 5.98; Cl, 15.03.

EXAMPLE 2

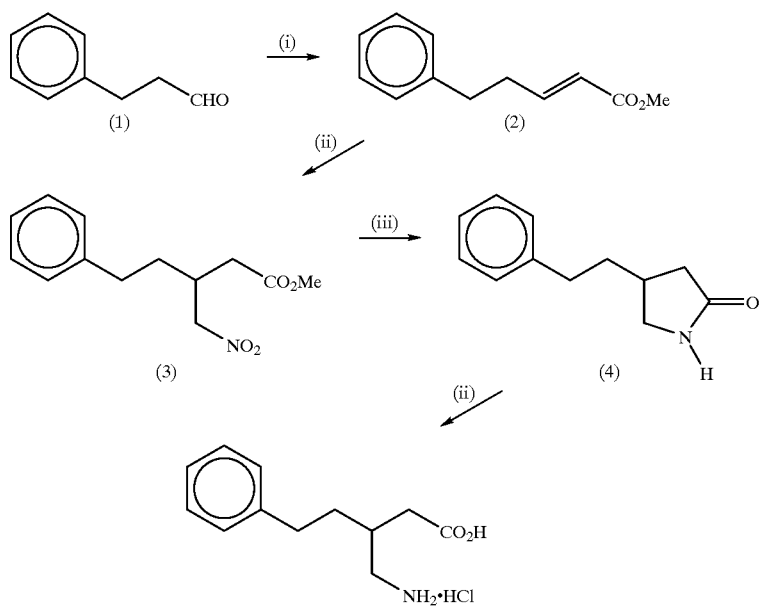

(i) MeO$_2$CCH═PPh$_3$, THF, 40° C.;
(ii) MeNO$_2$, DBU;
(iii) Raney Nickel, H$_2$, MeOH;
(iv) 6N HCl

Synthesis of the Unsaturated Ester (2)

Hydrocinnamaldehyde (2.0 g, 14.9 mmol) was dissolved in dry tetrahydrofuran (50 mL) and heated to reflux with methyl (triphenyl-phosphoranylidene) acetate (5.0 g, 14.9 mmol). After 6 hours the solvent was removed in vacuo and the residue stirred with n-pentane (75 mL). After 1 hour the solid was removed by filtration and the solvent removed in vacuo. The residue was purified by flash chromatography (silica, ethyl acetate/heptane 1:9) to give 2.24 g (79%) of (2) as a colorless oil.

$^1$H NMR (400 MHz) (CDCl$_3$): δ 2.53 (2H, m), 2.77 (2H, m), 3.72 (3H, s), 5.84 (1H, d, J=16 Hz), 6.98 (1H, m), 7.18 (3H, m), 7.27 (2H, m). IR (thin film) (cm$^{-1}$) v: 978, 1038, 1044, 1150, 1175, 1203, 1272, 1319, 1436, 1658, 1724, 1950.

MS (CI$^+$)(m/z): 191 (MH$^+$, 100%), 159 (55%), 130 (40%), 117 (51%). Microanalysis calculated for C$_{12}$H$_{14}$O$_2$: C, 75.76; H, 7.42; N, 0.0. Found: C, 75.54; H, 7.32; N, <0.3.

Synthesis of the Nitroester (3)

The unsaturated ester (2) (1.02 g, 5.37 mmol) was dissolved in nitromethane (20 mL) and stirred at room temperature with 1,8-diazabicyclo[5.4.0]undec-7-ene (803 μL, 5.37 mmol). After 5 hours the mixture was diluted with diethyl ether (100 mL) and washed with water (40 mL) and then 2N HCl (2×40 mL) followed by brine (40 mL). The organic phase was collected, dried (MgSO$_4$), and the solvent removed in vacuo. The residue was purified by flash chromatography (silica ethyl acetate/heptane 3:7) to give 959 mg (71%) of (3) as a colorless oil.

$^1$H NMR (400 MHz) (CDCl$_3$): δ 1.77 (2H, m), 2.51 (2H, d, J=6 Hz), 2.67 (3H, m), 3.70 (3H, s), 4.52 (2H, m), 7.15 (2H, m), 7.20 (1H, m), 7.28 (2H, m). IR (thin film) (cm$^{-1}$l) v: 751, 1003, 1179, 1384, 1435, 1455, 1496, 1557, 1603, 1732, 2953. MS (Cl$^+$)(m/z): 252 (MH$^+$, 29%), 220 (100%), 129 (83%). Microanalysis calculated for C$_{13}$H$_{17}$NO$_4$: C, 62.14; H, 6.82; N, 5.57. Found: C, 62.16; H, 6.72; N, 5.82.

Synthesis of the Lactam (4)

The nitro ester (937 mg, 3.7 mmol) was dissolved in methanol (25 mL) and shaken over Raney Nickel (prewashed with methanol, catalytic) under an atmosphere of hydrogen gas (35 psi) at 35° C. After 5 hours the mixture was filtered through celite to remove the catalyst. The solvent was removed in vacuo and the residue purified by flash chromatography (silica, ethyl acetate/heptane 6:4 then ethyl acetate/methanol 9:1) to give 563 mg (80%) of (4) as an oil which solidified on standing.

$^1$H NMR (400 MHz) (CDCl$_3$): δ 1.82 (2H, m), 2.05 (1H, m), 2.47 (2H, m), 2.64 (2H, m), 3.05 (1H, m), 3.48 (1H, m), 5.66 (1H, br s), 7.14–7.23 (3H, m), 7.28 (2H, m). IR (thin film) (cm$^{-1}$) v: 749, 1069, 1271, 1296, 1364, 1421, 1455, 1493, 1601, 1683, 2928, 3197. Microanalysis calculated for C$_{12}$H$_{15}$NO: C, 76.16; H, 7.99; N, 7.40. Found: C, 76.23; H, 7.87; N, 7.63.

Synthesis of 3-aminomethyl-5-phenyl-pentanoic acid

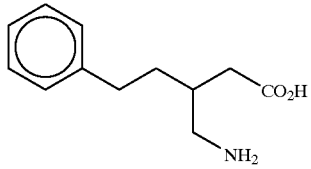

The lactam (4) (331 mg, 1.75 mmol) was heated to reflux in 6N HCl (20 mL). After 5 hours the mixture was cooled to room temperature and the solvent removed in vacuo. The residue was triturated with ethyl acetate to give a white solid. This was collected and dried to give 380 mg (89%) of the product as a white powder.

$^1$H NMR (400 MHz) (d$_6$-DMSO): δ 1.55 (1H, m), 1.70 (1H, m), 2.09 (1H, m), 2.41 (2H, m), 2.59 (2H, m), 2.85 (2H, m), 7.14–7.33 (5H, m), 8.06 (3H, br s). Microanalysis calculated for C$_{12}$H$_{18}$NO$_2$Cl: C, 59.14; H, 7.44; N, 5.75. Found: C, 58.90; H, 7.43; N, 5.67.

What is claimed is:

1. The compounds of Formula I

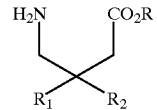

or a pharmaceutically acceptable salt thereof wherein:

R is hydrogen or lower alkyl;

R$_1$ is hydrogen or lower alkyl;

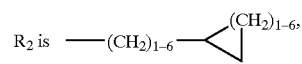

straight or branched alkyl of from 8 to 11 carbons,

—(CH$_2$)$_{(1-4)}$—X—(CH$_2$)$_{(0-4)}$-phenyl, wherein X is —O—, —S—, —NR$_3$— wherein R$_3$ is alkyl of from 1 to 6 carbons, cycloalkyl of from 3 to 8 carbons, benzyl, phenyl, wherein phenyl and benzyl can be unsubstituted or substituted with from 1 to 3 substituents each independently selected from alkyl, alkoxy, halogen, hydroxy, carboxy, carboalkoxy, trifluoromethyl, amino, and nitro.

2. A compound according to claim 1 wherein R$_1$ is hydrogen or methyl; and

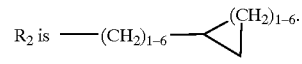

3. A compound according to claim 1 wherein R$_1$ is hydrogen or methyl and

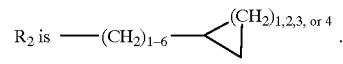

4. A compound according to claim 1 wherein

R$_1$ is hydrogen or methyl; and

R$_2$ is (CH$_2$)$_{1-4}$—X—(CH$_2$)$_{0-4}$-phenyl.

5. A compound according to claim 1 wherein

R$_1$ is hydrogen or methyl and

R$_2$ is (CH$_2$)$_1$—S—(CH$_2$)$_{0-4}$-phenyl.

6. A compound according to claim 1 wherein

R$_1$ is hydrogen or methyl; and

R$_2$ is straight or branched alkyl of from 8 to 11 carbons.

7. A compound according to claim 1 and selected from

3-Aminomethyl-4-cyclohexyl-butyric acid;

3-Aminomethyl-5-phenyl-pentanoic acid;

3-Aminomethyl-5-benzylsulfanyl-pentanoic acid;

3-Aminomethyl-5-(4-bromo-benzylsulfanyl)-pentanoic acid;

3-Aminomethyl-5-(3,4-dichloro-benzylsulfanyl)-pentanoic acid;

5-(4-Amino-benzyloxy)-3-aminomethyl-pentanoic acid;

3-Aminomethyl-5-(4-trifluoromethyl-phenylsulfanyl)-pentanoic acid;

3-Aminomethyl-5-p-tolylsulfanyl-pentanoic acid;

3-Aminomethyl-4-[2-(4-chloro-phenyl)-ethylsulfanyl]-butyric acid;

3-Aminomethyl-4-[2-(2,4-dichloro-phenyl)-ethylsulfanyl]-butyric acid;

3-Aminomethyl-4-(4-methyl-benzylsulfanyl)-butyric acid;

3-Aminomethyl-4-(4-bromo-phenylsulfanyl)-butyric acid;

3-Aminomethyl-4-(3,4-dichloro-benzylsulfanyl)-butyric acid;

3-Aminomethyl-4-cyclobutyl-butyric acid hydrochloride;

3-Aminomethyl-4-cyclopropyl-butyric acid; and

3-Aminomethyl-4-(4-tert-butyl-phenoxy)-butyric acid.

8. A pharmaceutical composition comprising a therapeutically effective amount of a compound according to claim 1 and a pharmaceutically acceptable carrier.

9. A method for treating epilepsy comprising administering a therapeutically effective amount of a compound according to claim 1 to a mammal in need of said treatment.

10. A method for treating faintness attacks, hypokinesia, and cranial disorders comprising administering a therapeutically effective amount of a compound according to claim 1 to a mammal in need of said treatment.

11. A method for treating neurodegenerative disorders comprising administering a therapeutically effective amount of a compound according to claim 1 to a mammal in need of said treatment.

12. A method for treating depression comprising administering a therapeutically effective amount of a compound according to claim 1 to a mammal in need of said treatment.

13. A method for treating anxiety comprising administering a therapeutically effective amount of a compound according to claim 1 to a mammal in need of said treatment.

14. A method for treating panic comprising administering a therapeutically effective amount of a compound according to claim 1 to a mammal in need of said treatment.

15. A method for treating pain comprising administering a therapeutically effective amount of a compound according to claim 1 to a mammal in need of said treatment.

16. A method for treating neuropathological disorders comprising administering a therapeutically effective amount of a compound according to claim 1 to a mammal in need of said treatment.

17. A method for treating inflammation comprising administering a therapeutically effective amount of a compound according to claim 1 to a mammal in need of said treatment.

18. A method for treating gastrointestinal damage comprising administering a therapeutically effective amount of a compound according to claim 1 to a mammal in need of said treatment.

* * * * *